(12) United States Patent
Honaryar et al.

(10) Patent No.: US 8,961,394 B2
(45) Date of Patent: Feb. 24, 2015

(54) SELF-SEALING FLUID JOINT FOR USE WITH A GASTRIC BAND

(75) Inventors: Babak Honaryar, Orinda, CA (US); Sean Snow, Carpinteria, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 414 days.

(21) Appl. No.: 13/332,010

(22) Filed: Dec. 20, 2011

(65) Prior Publication Data

US 2013/0158343 A1    Jun. 20, 2013

(51) Int. Cl.
*A61F 2/04* (2013.01)

(52) U.S. Cl.
USPC .......................................................... 600/37

(58) Field of Classification Search
CPC ............... A61F 5/005–5/0066; A61F 5/0076; A61F 5/003; A61F 5/0033; A61M 16/0816; A61M 16/0875; F16L 17/06; F16L 21/00–21/08; F16L 23/00–23/24; F16L 31/00–31/02; F16L 37/06
USPC .................. 600/37; 137/247.11–247.51, 384; 128/120, 126, 155; 285/10–11, 80, 285/95–113, 405–416; 606/151–158
See application file for complete search history.

(56) References Cited

U.S. PATENT DOCUMENTS

| | | |
|---|---|---|
| 1,174,814 A | 3/1916 | Brennan et al. |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

(Continued)

*Primary Examiner* — Catherine B Kuhlman
(74) *Attorney, Agent, or Firm* — Gordon & Jacobson, PC (57) ABSTRACT

Generally described herein are apparatus, systems and methods related to a mechanical interlock joint geometry for various components and joining of components thereby creating a reliable seal against fluid leaks that is resistant at typical pressures experienced when the components are implanted into a human body. Furthermore, the seal may be enhanced when a fluid pressure exerted inside the components is increased (e.g., from 1 to 10 psi).

27 Claims, 7 Drawing Sheets

(56) References Cited

U.S. PATENT DOCUMENTS

| | | |
|---|---|---|
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,299,012 A | 11/1981 | Oetiker |
| 4,340,083 A | 7/1982 | Cummins |
| 4,399,809 A | 8/1983 | Baro et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | De Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,487 A | 7/1990 | Holtermann |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,091,171 A | 2/1992 | Yu et al. |
| 5,116,652 A | 5/1992 | Alzner |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,330,448 A | 7/1994 | Chu |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A | 8/1997 | Vincent et al. |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,766,232 A | 6/1998 | Grevious et al. |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,372,494 B1 | 4/2002 | Naughton et al. |
| 6,383,218 B1 | 5/2002 | Sourdile et al. |
| 6,383,219 B1 | 5/2002 | Telandro et al. |
| 6,387,105 B1 | 5/2002 | Gifford, III et al. |
| 6,417,750 B1 | 7/2002 | Shon |
| 6,418,934 B1 | 7/2002 | Chin |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |

(56) References Cited

U.S. PATENT DOCUMENTS

| | | |
|---|---|---|
| 6,527,701 B1 | 3/2003 | Sayet et al. |
| 6,547,801 B1 | 4/2003 | Dargent et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredericks |
| 6,715,731 B1 | 4/2004 | Post et al. |
| 6,729,600 B2 | 5/2004 | Mattes et al. |
| 6,754,527 B1 | 6/2004 | Stroebel et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fischer et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Birk |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,204,821 B1 | 4/2007 | Clare et al. |
| 7,204,832 B2 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrum |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |

(56) References Cited

U.S. PATENT DOCUMENTS

| | | |
|---|---|---|
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Krundson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neil |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161139 A1 | 7/2006 | Levine et al. |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0129705 A1* | 6/2007 | Trombley et al. ............. 604/523 |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gartner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0103476 A1* | 5/2008 | Schulte ..................... 604/500 |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0191466 A1* | 8/2008 | Knipple et al. ............. 285/31 |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |

(56) References Cited

U.S. PATENT DOCUMENTS

| | | |
|---|---|---|
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2010/0010291 A1 | 1/2010 | Birk et al. |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0201874 A1 | 8/2011 | Birk et al. |
| 2011/0207995 A1 | 8/2011 | Snow |
| 2011/0313240 A1* | 12/2011 | Phillips et al. .................. 600/37 |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2074972 | 7/2009 |
| EP | 2095796 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | 96-14894 | 5/1996 |
| WO | 9614894 A1 | 5/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09049 | 2/2000 |
| WO | WO 00/15158 | 3/2000 |
| WO | 00-61981 | 10/2000 |
| WO | 0061981 A1 | 10/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |

(56) References Cited

FOREIGN PATENT DOCUMENTS

| WO | WO 03/059215 | 7/2003 |
|---|---|---|
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Adrian et al.; "Mechanism of Pancreatic Polypeptide Release in Man." The Lancet; pp. 161-163; Jan. 22, 1977.

Anson; "Shape Memory Alloys—Medical Applications," Source: Materials World, vol. 7, No. 12, pp. 745-747, Dec. 1999.

Asakawa et al; "Antagonism of Ghrelin Receptor Reduces Food Intake and Body Weight Gain in Mice"; Gut.; V.52; pp. 947-952; 2003.

Baggio et al. "Biology of Incretins: GLP-1 and GIP"; Gastroenrology; V. 132; pp. 2131-2157; 2007.

Ballantyne; "Peptide YY(1-36) and Peptide YY(3-36): Part I. Distribution, Release, and Actions"; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; "Physiology"; V. 5; pp. 55-57, 210, 428, 540, 554, 579, 584, 591; 2004.

BioEnterics Lap-Band Adjustable Gastric Banding System, Inamed Health, pub., pp. 1-115; Aug. 28, 2003.

Boulant et al.; "Cholecystokinin in Transient Lower Oesophageal Sphincter Relaxation Due to Gastric Distension in Humans"; Gut.; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Brown et al; "Symmetrical Pouch Dilation After Laparoscopic Adjustable Gastric Banding: Incidence and Management"; Obesity Surgery; V. 18, pp. 1104-1108; 2008.

Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Chaptini et al.; "Neuroendocrine Regulation of Food Intake"; Current Opinion in Gastroenterology; V. 24; pp. 223-229; 2008.

Chaudhri; "Can Gut Hormones Control Appetite and Prevent Obesity?" Diabetes Care; V. 31;.Supp 2; pp. S284-S289; Feb. 2008.

Cohen et al.; "Oxyntomodulin Suppresses Appetite and Reduces Food Intake in Humans"; J. Clin. Endocrinol. Metab.; V. 88; No. 10; pp. 4696-4701; 2003.

Corno et al.; "A new implantable device for telemetric control of pulmonary blood flow"; New ideas; received Apr. 24, 2004; received in revised form Jul. 12, 2002; 10 pages.

Corno et al.; "FlowWatchTM in clipped and inclipped position"; Interact Cardio Vase Thorac Surg 2002; 1:46-49; Copyright @ 2002 The European Association for Cardio-thoracic Surgery; 1 page.

Cummings et al.; "Plasma Ghrelin Levels After Diet-Induced Weight Loss or Gastric Bypass Surgery"; N. Engl J. Med; V. 346, No. 21; pp. 1623-1630; May 23, 2002.

Cummings; "Gastrointestinal Regulation of Foot Intake"; The Food Journal of Clinical Investigation; V. 117, N. 1; pp. 13-23; Jan. 2007.

Dakin et al.; "Oxyntomodulin Inhibits Food Intake in the Rat"; Endocrinology; V. 142; No. 10; pp. 4244-4250; 2001.

Dakin et al.; "Peripheral Oxyntomodulin Reduces Food Intake and Body Weight gain in Rats"; Endocrinology; V. 145; No. 6; pp. 2687-2695; Jun. 2004.

Davison; "Activation of Vagal-Gastric Mechanoreceptors by Cholecystokinin"; Proc. West. Pharmocol. Soc.; V. 29; pp. 363-366; 1986.

De Waele et al.; "Endoscopic Volume Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; "Molecular Weight of Heparin Using 13C Nuclear Magnetic Resonance Spectroscopy" Journal of Pharmaceutical Science, V. 84, I 2; 1995, Abstract only.

Dixon et al.; "Pregnancy After Lap-Band Surgery: Management of the Band to Achieve Healthy Weight Outcomes"; Obesity Surgery; V. 11, pp. 59-65; 2001.

Doldi et al.; "Intragastric Balloon: Another Option for Treatment of Obesity and Morbid Obesity"; Hepato-Gastroenterology; V. 51, N. 55; pp. 294-307; Jan-Feb 2004.

Doldi et al.; "Treatment of Morbid Obesity with Intragastric Balloon in Association with Diet"; Obesity Surgery; V. 10, pp. 583-587; 2000.

Doldi et al; "Intragastric Balloon in Obese Patients"; Obesity Surgery; V. 10, 578-581; 2000.

Ekblad et al.; "Distribution of Pancreatic Peptide and Peptide-YY"; Peptides; V. 23; pp. 251-261; 2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

Galloro et al; "Preliminary Endoscopic Technical Report of an New Silicone Intragastric Balloon in the Treatment of Morbid Obesity"; Obesity Surgery; V. 9, pp. 68-71; 1999.

GinShiCel MH Hydroxy Propyl Methyl Cellulose, Web Page http://www.ginshicel.cn/MHPC.html, Nov. 12, 2008.

Girard; "The incretins: From the concept to their use in the treatment of type 2 diabetes. Part A: Incretins: Concept and physiological functions"; Diabetes and Metabolism; V. 34; pp. 550-559; 2008.

Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.

Grise et al.; "Peptide YY Inhibits Growth of Human Breast Cancer in Vitro and in Vivo"; Journal of Surgical Research; V. 82; pp. 151-155; 1999.

Grundy; "Signaling the State of the Digestive Tract"; Autonomic Neuroscience: Basic and Clinical; V. 125; pp. 76-80; 2006.

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al.; "Gut hormones and appetite control." Oral Diseases; V. 15; pp. 18-26; 2009.

(56) References Cited

OTHER PUBLICATIONS

Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Helioscopie Product Insert for Heliogast, 1 page; Jun. 2009.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J. Gastrointest Surg.; V. 13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; "Processing and metabolism of Peptide-YY: Pivotal roles of Dipeptidase-IV, Aminopeptidase-P, and Endopeptidase-24.11"; Endocrinology; V. 134, No. 5; pp. 2088-2094; 1994.
Naslund et al. "Pranidal subcutaneous injections of glucagon-like peptide-1 cause weight loss in obese human subjects"; British Journal of Nutrition; V. 91; pp. 439-446; 2004.
Neary et al.; "Peptide YY(3-36) and Glucagon-Like Peptide-$1_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Potier et al.; "Protein, amino acids, and the control of food intake"; Current Opinion in Clinical Nutrition and Metabolic Care; V. 12; pp. 54-58; 2009.
Qjan et al.; "Pulmonary delivery of a GLP-1 receptor agonist, BMS-686117"; International Journal of Pharmaceutics; V. 366; pp. 218-220; 2008.
Rang et al.; "Pharmacology"; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. "Peptide YY: A Potential Therapy for Obesity"; Current Drug Targets; V. 6; pp. 171-179; 2005.
Sannino et al.; "Crosslinking of Cellulose Derivatives and Hyaluronic Acid with Water-Soluble Carbodiimide" Polymer 46; pp. 11206-11212; 2005.
Shechter et al.; "Reversible PEGylation of peptide YY3-36 prolongs its inhibition of food intake in mice"; FEBS Letters; V. 579; pp. 2439-2444; 2005.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
Silver et al.; "Physical Properties of Hyaluronic Acid and Hydroxypropylmethylcellulose in Solution: Evaluation of Coating Ability" Journal of Applied Biomaterials, V. 5; pp. 89-98, 1994.
Small et al.; "Gut hormones and the control of appetite"; TRENDS in Endocrinology and Metabolism; V. 15. No. 6; pp. 259-263; Aug. 2004.
Stanley et al.; "Gastrointestinal Satiety Signals III. Glucagon-like Peptide 1, oxyntomodulin, peptide YY, and Pancreatic polypeptide"; Am. J. Physiol Gastrointest Liver Physiol; V. 286; pp. 693-697; 2004.
Tezel; "The Science of Hyaluronic Acid Dermal Fillers," Journal of Cosmetic and Laser Therapy (2008) 10: pp. 35-42.
Tolhurst et al.; "Nutritional regulation of glucagon-like peptidel secretion"; J. Physiol.; V. 587, No. 1; pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.
Wahlen et al.; "The BioEnterics Intragastric Balloon (BIB): How to Use It"; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; "Preparation of Extremely Obese Patients for Laparoscopic Gastric Banding by Gastric Balloon Therapy"; Obesity Surgery; V. 9, pp. 261-264, 1999.
Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
Yuzuriha et al.; "Gastrointestinal Hormones (anorexigenic peptide YY and orexigenic ghrelin) influence neural tube development"; Faseb J.; V. 21; pp. 2108-2112; 2007.

\* cited by examiner

SELF-SEALING FLUID JOINT FOR USE WITH A GASTRIC BAND

FIELD

The present invention generally relates to medical systems, devices and uses thereof for treating obesity and/or obesity-related diseases. More specifically, the present invention relates to a mechanical interlock joint geometry for connecting two components.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND APO (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

These gastric banding systems may include components such as a gastric band, an access port, fluid reservoirs and tubing to connect the various aforementioned components. Typically, these implantable components can contain or carry fluid at pressures up to about 12 psi, and are constructed out of special grades of silicone rubber for biocompatibility reasons. Metal or plastic barbed connectors are used to connect these implantable components to one another or to the tubing. These barbed connectors function well with rubber parts of higher durometer (e.g., 70 Shore A durometer or higher) but suffer from a low "pull-out" force resulting in slippage and separation of the rubber part from the barbed connected for lower durometer rubber components. This connection issue has traditionally been addressed by a number of techniques such as using an adhesive to secure the joint, overmolding the rubber on top of the hard connector to create a stronger rubber-to-connector bond, using a screw geometry or a barbed connector against the high durometer rubber, or compression fitting.

However such approaches have various drawbacks. For example, using an adhesive is undesirable due to the difficulties in controlling the amount delivered and the degree of cure for proper strength. Moreover, the adhesive might not be biocompatible.

Employing overmolding is also problematic as it is expensive and requires a metal insert which may agitate the surrounding internal organs of the patient.

Adding a screw geometry increases the cost of the system and fails to guarantee a fluid-tight seal under pressure. In addition, the rubber requires higher durometer materials due to the required structural rigidity.

Using a barbed connector also adds cost and complexity, in addition to the above-discussed agitation possibility of internal organs due to the rigidity of the materials. Furthermore, the barbed connector may still be limited for use with only high durometer rubbers since the rubber-connector contact might not generate enough resistance against a pull-out force when using a softer rubber. Fatigue-stresses at the rubber-connector junction would also remain an issue under this approach.

Compression fittings are bulky, expensive and hard to attach during a laproscopic surgical procedure.

Figure 1:
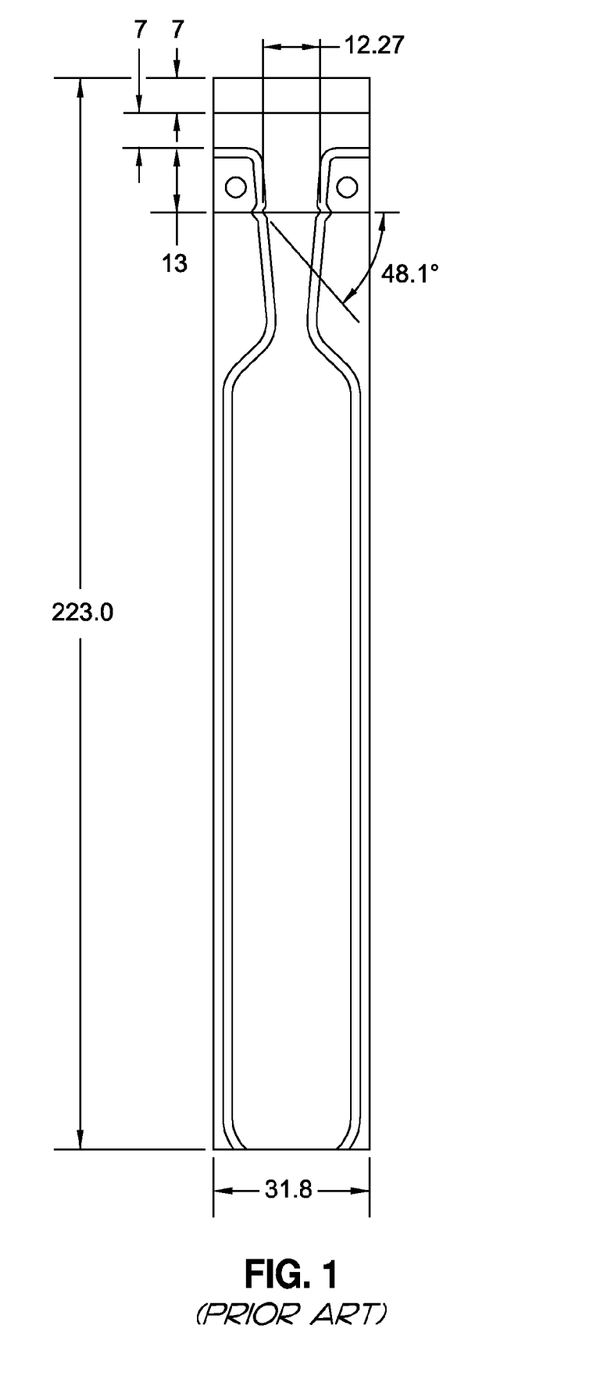
FIG. 1 illustrates a prior art self-sealing container.

Fusco, U.S. Patent Pub. No. 2009/0220176, discloses an application for filling polyethylene bags for the food industry, which is tangentially related in that it is also geared towards sealing. However, the system of Fusco as illustrated in FIG. 1 does not appear usable in a human body. Furthermore, the system of Fusco is structurally and functionally different than the present invention.

As a result, none of these options are particularly attractive in effectively connecting two rubber components.

Accordingly, what is needed is a connection technique that creates a reliable seal against fluid leaks at typical pressures appropriate for implantation into a human body.

SUMMARY

Generally described herein are apparatus, systems and methods related to a mechanical interlock joint geometry for various components and joining of components thereby creating a reliable seal against fluid leaks resistant at typical pressures experienced when the components are implanted into a human body. Furthermore, the seal may be enhanced when a pressure is increased (e.g., from 1 to 10 psi). In other words, fluid pressure may even increase the seal contact pressure.

In one embodiment, provided is a gastric banding system for the treatment of obesity. The gastric banding system includes a gastric band having an inflatable portion and a ring, a first tube having a first end and a second end, the first end of the first tube connected to the inflatable portion, a fluid reservoir including two halves and a first interlock, the first half having a first ball and a first flange, and the second half defining a first ball receiving cavity for receiving the first ball, and further defining a first flange receiving cavity for receiving the first flange, wherein the two halves of the fluid reservoir form the first interlock when the first ball receiving cavity receives the first ball, and when the first flange receiving cavity receives the first flange, the fluid reservoir further having a first end and a second end, the first end of the fluid reservoir connected to the second end of the first tube, a second tube having a first end and a second end, the first end of the second tube connected to the second end of the fluid reservoir, and an access port connected to the second end of the second tube.

In one embodiment, provided is a fluid reservoir for carrying fluid within a gastric banding system for the treatment of obesity. The gastric banding system includes a first half of the fluid reservoir and a second half of the fluid reservoir. The first half of the fluid reservoir may include a first connector for fluidly connecting the fluid reservoir to an inflatable portion of a gastric band, a first housing coupled to the connector, the first housing defining a first sub-reservoir, the first housing tapering to a first flat joining surface, a ball and flange coupled to the first flat joining surface, the ball and flange defining a second sub-reservoir. The second half of the fluid reservoir may include a second connector for fluidly connecting the fluid reservoir to an access port, a second housing coupled to the second connector, the second housing defining a third sub-reservoir, the second housing tapering to a second flat joining surface, the second housing further defining a ball receiving cavity for receiving the ball and a flange receiving cavity for receiving the flange to interlock the first half of the fluid reservoir with the second half of the fluid reservoir.

In one embodiment, provided is a tube-to-tube apparatus for establishing a fluid path between a first tube and a second tube to allow the tubes to carry fluid within a gastric banding system for the treatment of obesity. The apparatus includes a first sleeve and a second sleeve. The first sleeve may include a first end overmolding the first tube, an intermediate portion coupled to the first end, the intermediate portion defining a first sub-reservoir and having a first flat joining surface, a second end having a ball and flange, the second end protruding from the first flat joining surface and defining a second sub-reservoir fluidly coupled to the first sub-reservoir. The second sleeve may be interlocked to the first sleeve and may include a first end of the second sleeve overmolding the second tube, an intermediate portion coupled to the first end of the second sleeve, the intermediate portion defining a third sub-reservoir and having a second flat joining surface, and a second end of the second sleeve defining a ball receiving cavity for receiving the ball and a flange receiving cavity for receiving the flange to interlock the first sleeve with the second sleeve.

BRIEF DESCRIPTION OF THE DRAWINGS

The features, obstacles, and advantages of the present invention will become more apparent from the detailed description set forth below when taken in conjunction with the drawings, wherein.

DETAILED DESCRIPTION

Apparatuses, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

While described generally herein with components of a gastric banding system, one of ordinary skill in the art will understand that the concepts are applicable to any scenario where sealing against leaks may be advantageous and is not meant to be limited to the scope of gastric banding systems.

The present invention generally provides mechanical interlock joint geometry for creating a reliable seal against fluid leaks at a range of pressures. Furthermore, the seal may be enhanced when a pressure is increased (e.g., from 1 to 10 psi). That is, fluid pressure may increase the seal contact pressure.

Figure 2:
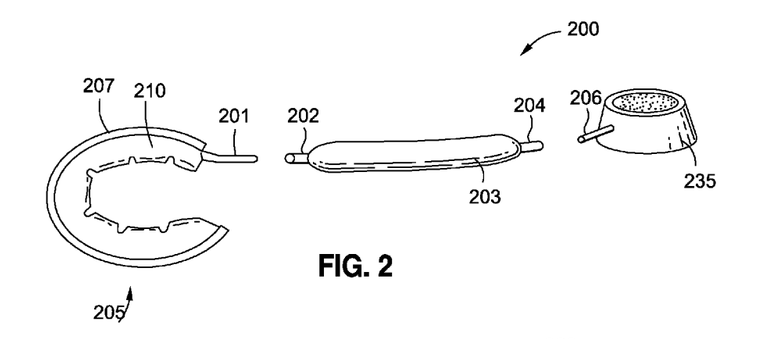
FIG. 2 illustrates a gastric banding system including various components according to an embodiment of the present invention.

One embodiment of the components of the gastric banding system 200 is illustrated in FIG. 2 and comprises a gastric band 205 coupled to a subcutaneous injection port 235 via a first tubing 202, a reservoir 203 and a second tubing 204. The gastric band 205 comprises a circular ring 207 and an inflatable portion 210 disposed on the inside of the ring 207. The inflatable portion 210 separates the patient's stomach from the ring 207 when the gastric band 205 is implanted around the esophageal-gastric junction of the patient's stomach. The ring 207 provides structure and support to the inflatable portion 210, and facilitates implanting the gastric band 205 around the patient's stomach.

The access port 235 may be sutured onto the rectus muscle sheath or any other conveniently accessible muscle. The rectus muscle sheath provides a secure surface on which to attach the access port 235 under a layer of fat that separates the patient's skin from the muscle.

The inflatable portion 210 may be filled and drained with a fluid via the reservoir 203. For example, the second tubing 204 may be connected to the subcutaneous access port 235 for filling and draining the inflatable portion 210 via subcutaneous injections. When more fluid is introduced in the inflatable portion 210, the constriction around the stomach generally becomes tighter. Correspondingly, when less fluid is present, the constriction loosens and/or opens up.

The fluids used within the gastric band 205 may include any fluid that is biocompatible and incompressible. The fluid has no adverse effect on the patient in the unlikely event that a leak emanates from the system. The fluid can simply be water or any biocompatible polymer oil such as caster oil. In an example embodiment, the fluid is saline, a drug, and/or combinations thereof.

Certain components (e.g., the first tubing 202, the reservoir 203 and the second tubing 204, etc.), including their structure and the joining to adjacent components thereof will now be described.

Figure 3A:
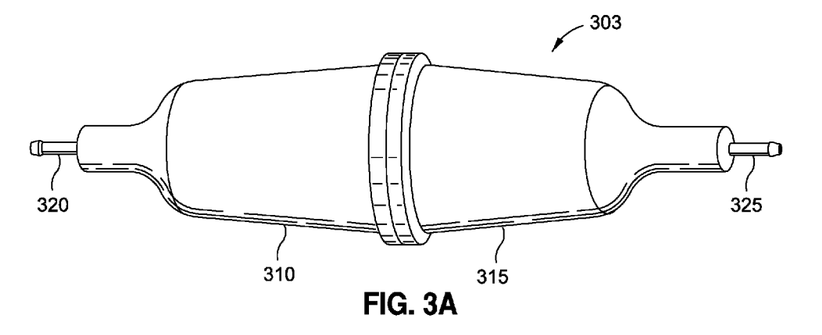
FIG. 3A illustrates a fluid reservoir according to an embodiment of the present invention.

FIG. 3A illustrates a fluid reservoir 303, which may be the reservoir 203 of FIG. 2, with other components of the gastric banding system removed for clarity. While described with respect to the gastric banding system, the assembly of the fluid reservoir 303 may be used in any implantable apparatus including obesity-controlling products. Here, the fluid reservoir 303 may include two halves, a male half 310 and a female half 315. The two halves 310 and 315 may be molded separately and then pushed or pressed together to create the fluid-tight fluid reservoir 303. No adhesive, external rings, clamps or other devices are necessary. In this example, the two halves 310 and 315 may be constructed out of silicone rubber of Shore A durometer of 50 or greater and may be molded over a pair of standard metal connectors 320 and 325, as the fluid reservoir 303 can be connected to an extruded tube. The metal connectors 320 and 325 may serve as an interface for transferring fluid into and out of the fluid reservoir 303.

Figure 3B:
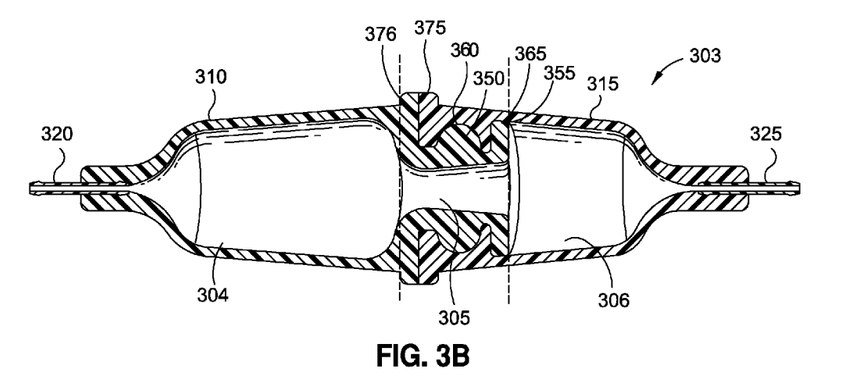
FIG. 3B illustrates a cross-sectional view of the fluid reservoir of FIG. 3A according to an embodiment of the present invention.

FIG. 3B illustrates a cross-sectional view of the fluid reservoir 303 of FIG. 3A. Here, the two halves 310 and 315 of the fluid reservoir 303 are illustrated to be interlocked via a ball 350 and a flange 355. That is, when the ball 350 and the flange 355 of the male half 310 are inserted and/or pushed into a ball receiving cavity 360 and a flange receiving cavity 365 of the female half 315, respectively, the flat, circumferential joining surface 376 and 375 of the male half 310 and the female half 315, respectively, are brought into contact to create the sealed fluid reservoir 303.

While the two halves 310 and 315 are utilized, the fluid reservoir 303 may actually be considered to comprise three sub-reservoirs joined together and in fluid communication. As previously described, the male half 310 of the fluid reservoir 303 defines both the first sub-reservoir 304 and the second sub-reservoir 305, which in turns leads into the third sub-reservoir 306 defined by the female half 315. The second sub-reservoir 305 may be proximal to the mating features which interlock to join the male half 310 and the female half 315. In one embodiment, the second sub-reservoir 305 is formed in the shape of an hour-glass.

Figure 3C:
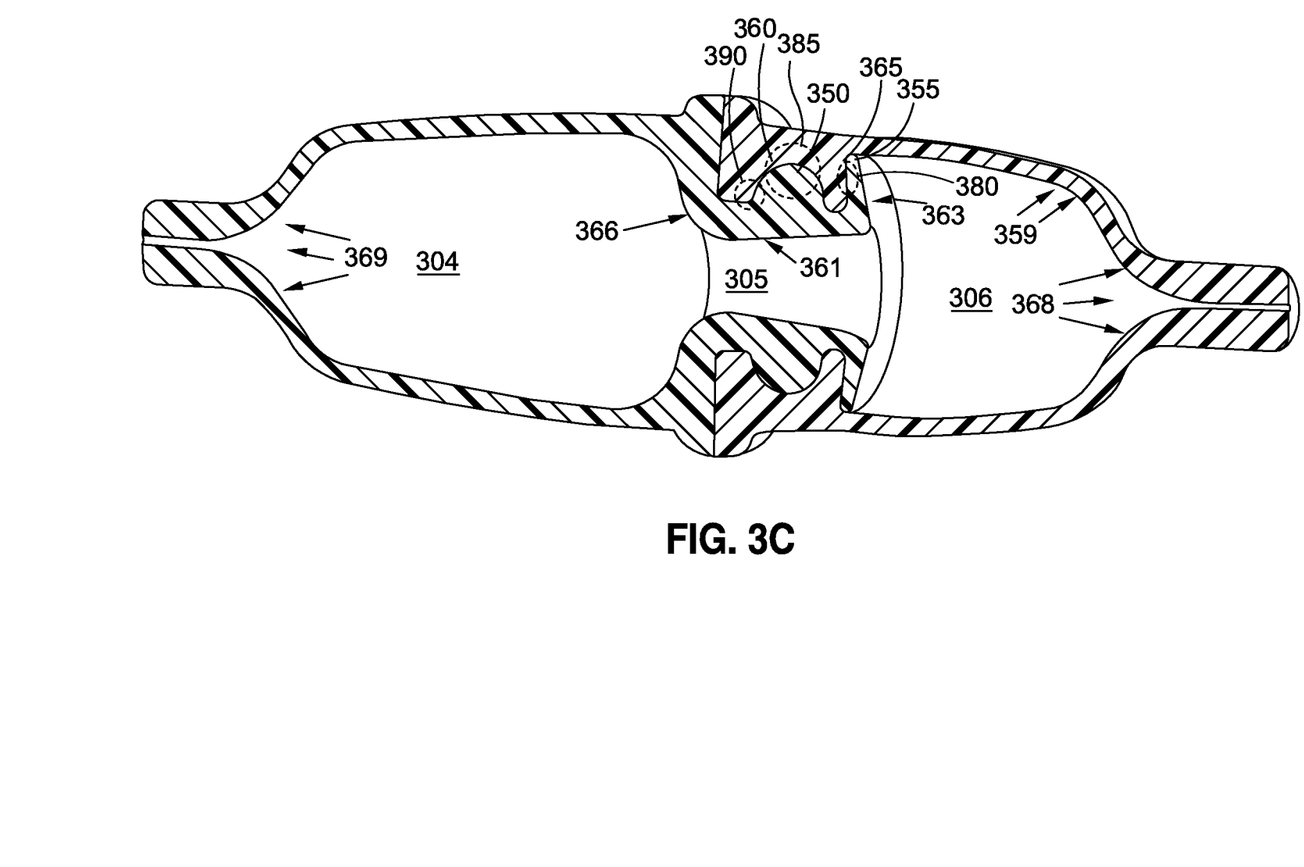
FIG. 3C illustrates a finite element analysis model of the fluid reservoir of FIG. 3A according to an embodiment of the present invention.

When assembled as shown in FIG. 3B, pressure introduced by the carrying of fluid within the first, second and third sub-reservoirs 304, 305 and 306 promotes the sealing capabilities of the fluid reservoir 303 as a whole. More particularly, as shown in FIG. 3C, three seals or sealing surfaces 380, 385 and 390 are enhanced or provided when the reservoir 303 is filled with fluid.

The first seal 380, which occurs between the flange 355 and the flange receiving cavity 365 is enhanced by forces illustrated by arrows 363, 368 and 369. More particularly, the fluid inside the third sub-reservoir 306 causes the force as shown by the arrow 363 to press the flange 355 against a wall of the flange receiving cavity 365 in the direction of arrow 363. In other words, by employing a flap-shaped geometry with respect to the flange 355, and having fluid only on one side of the flange 355, the seal is enhanced. Additionally, fluid inside the first sub-reservoir 304 causes forces in the direction of arrows 369 to further press the flange 355 against the wall of the flange receiving cavity 365. Furthermore, the forces illustrated by arrows 368 pulls the wall of the flange receiving cavity 365 even more tightly into the flange 355. In this manner, in addition to initial interference, the seal 380 is greatly enhanced when the reservoir 303 is filled with fluid (which is precisely when the seal 380 is needed to be enhanced to prevent leakage).

The second seal 385 is caused initially by the interference between the ball 350 and the ball receiving cavity 360. However, the second seal 385 is enhanced when fluid is present in the second sub-reservoir 305. The fluid in the second sub-reservoir 305 causes an upward pressure shown by arrow 361 pressing the ball 350 further into the ball receiving cavity 360. Noticeably, relatively-speaking, the ball receiving cavity 360 displaces less than the ball 350 because fluid in the third sub-reservoir 306 actually causes a slight bulge in the direction of 359 since the wall of the female half 315 is thinner at the location of arrows 359. In this manner, the fluid within the second and third sub-reservoirs 305 and 306 enhance the seal between the ball 350 and the ball receiving cavity 360.

The third seal 390 is caused, in one embodiment, by opposing forces in directions shown by arrows 368 and 369. In other words, the pressure that tries to pull the male half 310 and the female half 315 of the reservoir 303 apart actually generates a better fluid seal at the joint created by the ball 350 and the ball receiving cavity 360. Moreover, the force illustrated by arrow 363 exerts and further press the ball 350 into the contacting wall portions of the ball receiving cavity 360. In addition, the ball 350 creates a wedge effect, which only further assists the sealing process.

The semi-sphere shaped ball 350 may provide the advantage of easier assembly. However, other shapes are possible, which may provide other advantages. For example, as shown in FIGS. 6 and 7, configurations such as trapezoid and/or a triangle are illustrated.

Figure 6:
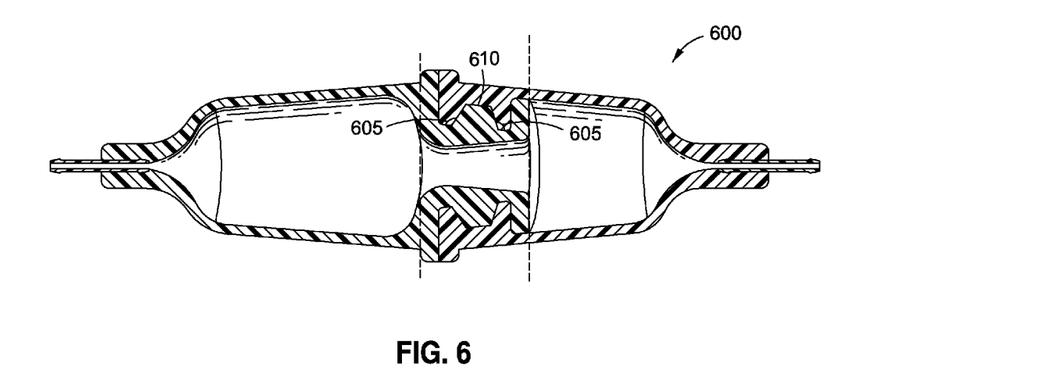
FIG. 6 illustrates a fluid reservoir having a trapezoidal-shaped element according to an embodiment of the present invention.

The configuration of FIG. 6 illustrates a fluid reservoir 600 having a trapezoid-shaped engaging element 610 in place of the ball-shaped engaging element (e.g., ball 350 of FIG. 3). The trapezoid-shaped engaging element 610 may be formed to include angles 605 in the range of between 92-135 degrees. By having an angle closer to about 92 degrees, the mechanical advantage provided by the wedge effect may be maximized.

Figure 7:
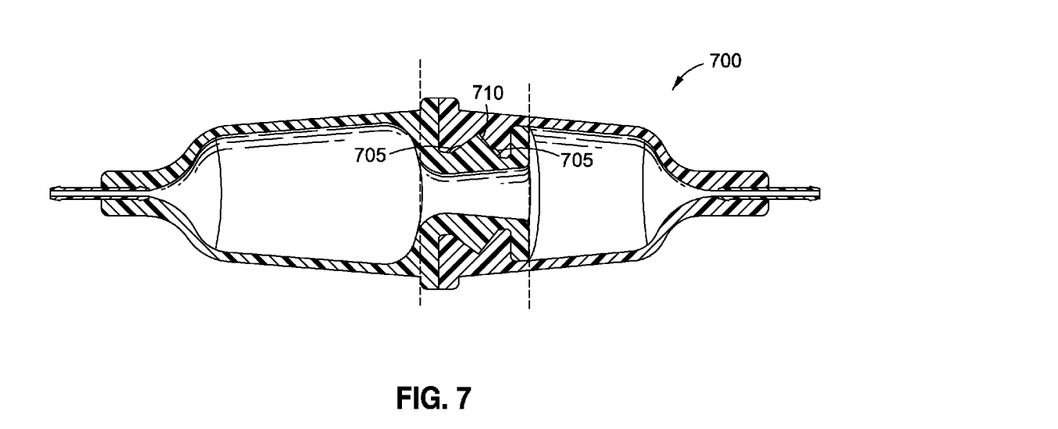
FIG. 7 illustrates a fluid reservoir having a triangular-shaped element according to an embodiment of the present invention.

The configuration of FIG. 7 illustrates a fluid reservoir 700 of yet another shape. Here, the fluid reservoir 700 has a triangular-shaped engaging element 710 in place of the ball-shaped engaging element (e.g., ball 350 of FIG. 3). Similar to the trapezoidal-shaped engaging element 610 of FIG. 6, the triangular-shaped engaging element 710 may be formed to include angles 705 in the range of between 92-135 degrees to improve the mechanical advantage and hence, the seal.

Figure 3D:
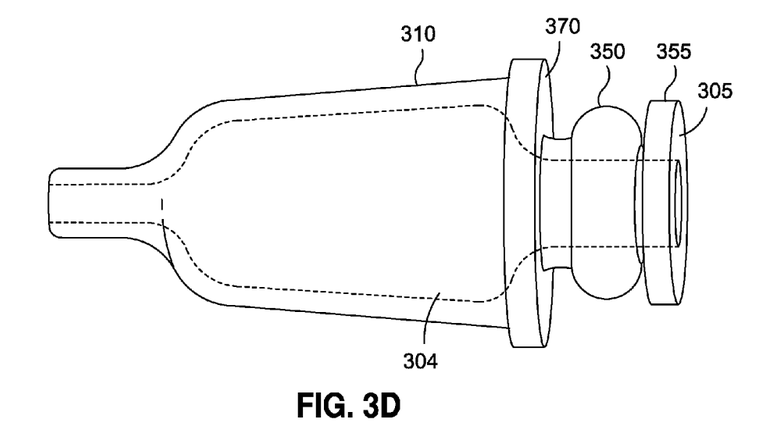
FIG. 3D illustrates the structure of a first half of the fluid reservoir of FIG. 3A according to an embodiment of the present invention.
Figure 3E:
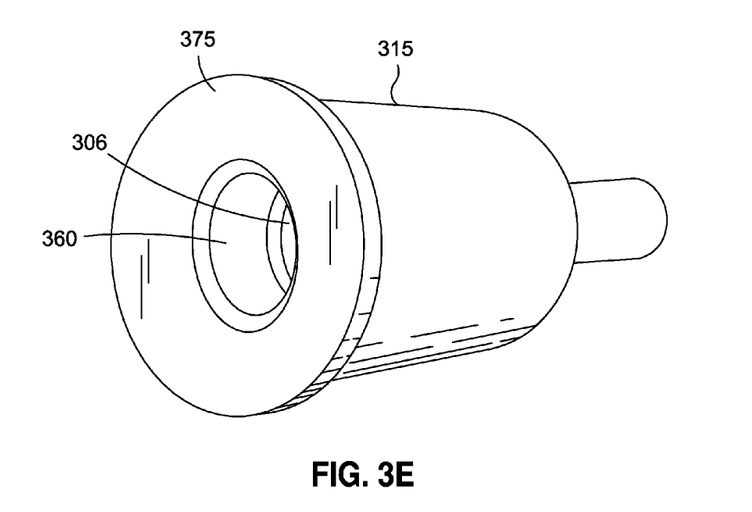
FIG. 3E illustrates the structure of a second half of the fluid reservoir of FIG. 3A according to an embodiment of the present invention.

Referring back to the fluid reservoir 303, FIGS. 3D and 3E illustrate the male half 310 and the female half 315 of the reservoir 303 separated for clarity. As shown in FIG. 3D, the male half 310 may be molded and may include a "bottle-shaped" housing portion defining the first sub-reservoir 304 outwardly tapering to a flat, circumferential joining surface 370 which is integrated, on the other side, to the ball 350 and flange 355 which not only serves as mating members but defines on its interiors the second sub-reservoir 305. This male half 310 may be molded out of silicone rubber and may stretch to allow the core of the mold to be pulled out from the larger hole on the connection side.

The female half 315 of the reservoir 303 illustrated in FIG. 3E may include a similar "bottle-shaped" portion defining the third sub-reservoir 306 outwardly tapering to a flat circumferential joining surface 375, which is of equal diameter to the circumferential joining surface 370 of the male half 310. The female half 315 may include the female mating members including the ball receiving cavity 360 and the flange receiving cavity 365 hidden from view, and may also be constructed out of silicone rubber or other appropriate materials and may be molded despite undercut features.

While the above-described mating technique to create an enhanced seal has been discussed thus far in relationship with a fluid reservoir, such embodiments are mere examples and the applicability of the concepts may be applied to other devices or apparatuses including other portions of the gastric banding system.

For instance, the interlocking geometry may be used to connect two extruded silicone tubes to avoid the usage of barbed or compression fitting.

Figure 4A:
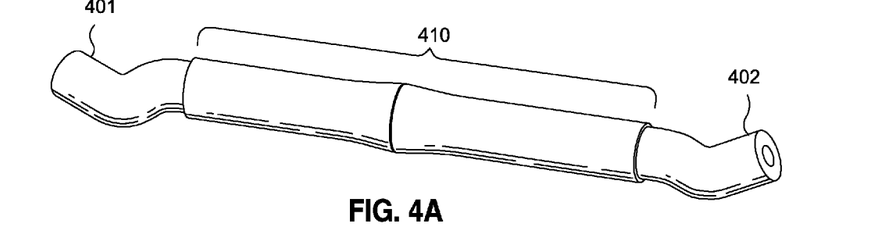
FIG. 4A illustrates a tubing according to an embodiment of the present invention.

FIG. 4A illustrates how a tube 401 may be connected to another tube 402 using an over-molded sleeve 410. The extruded tubes 401 and 402 can be as long as desired, but are shown truncated in FIG. 4A for clarity. The tube 401, for example, may be connected to an inflatable portion of a gastric band while the tube 402 may be a connecting tube of a reservoir or an access port. More particularly, the tubes 401 and 402 may be extruded and might not itself incorporate the interlocking geometry. Instead, as shown in the cross-sectional view of FIG. 4B, the tubes 401 and 402 may be connected to the sleeve 410, which may comprise a male sleeve 411 and a female sleeve 412, which are interlocked together via similar geometry as discussed above with respect to the fluid reservoir of FIG. 3. Since the sleeve is overmolded on the tubes 401 and 402, adhesives are not required to attach the tubes 401 and 402 to their respective ends of the sleeve 410.

Figure 4B:
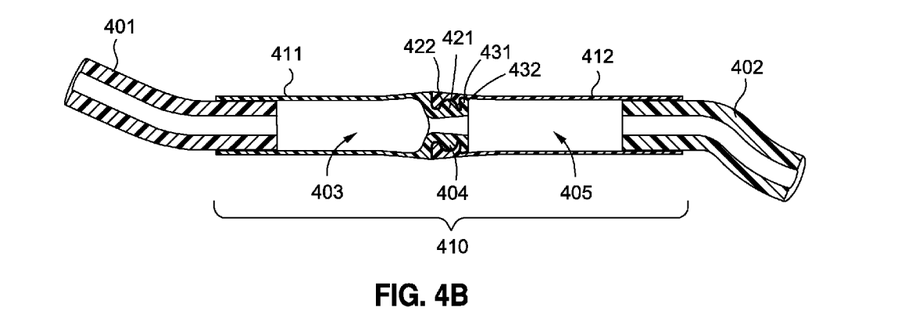
FIG. 4B illustrates a cross-sectional view of the tubing of FIG. 4A according to an embodiment of the present invention.

As far as the interlocking geometry is concerned, the proportions may be smaller in the sleeve 410 as compared to the fluid reservoir 303 of FIG. 3, but similarly, three sub-reservoirs are established to create the forces that enhance the sealing ability at the interlock.

Figure 4C:
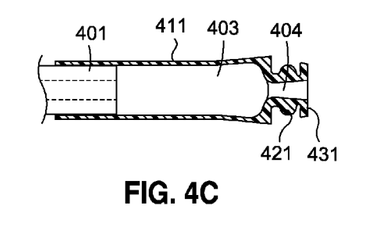
FIG. 4C illustrates a close-up view of a portion of the tubing of FIG. 4A according to an embodiment of the present invention.

FIG. 4C illustrates a close-up view of the connection between the extruded tube 401 and the male sleeve 411. The male sleeve 411 may be a single structural component and hollowed out and overmolded on the tube 401 at one end defining the first sub-reservoir 403 and the second sub-reservoir 404. The first sub-reservoir 403 may lead directly into an opening of the tube 401. Depending on the size of the first sub-reservoir 403 desired, the portion of the tube 401 that is overmolded by the male sleeve 411 may be configured. In addition, the length of the tube 401 that is overmolded may also impact lateral flexibility, such that more flexibility may be achieved where the overmolded area is minimized.

Figure 4D:
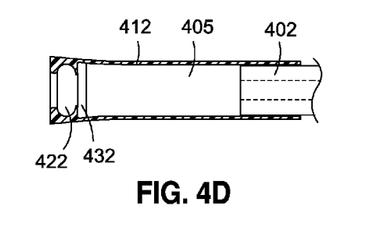
FIG. 4D illustrates a close-up view of a portion of the tubing of FIG. 4A according to an embodiment of the present invention.

FIG. 4D illustrates a close-up view of the connection between extruded tube 402 and the female sleeve 412. The female sleeve 412 may be a single structural component and hollowed out and overmolded on the tube 402 at one end defining the third sub-reservoir 405. The third sub-reservoir 405 may lead directly into an opening of the tube 402. Similarly, depending on the size of the third sub-reservoir 405 desired, the portion of the tube 402 that is overmolded by the female sleeve 412 may be configured, which in turn may also impact lateral flexibility.

Alternatively, or in addition, a tube-to-tube connection may be made without the over-molded sleeves. For example, a first tube may be molded to have the male features (e.g., ball and flange) while a second tube may be molded to have the female features (e.g., ball receiving cavity and the flange receiving cavity). By pressing the male features of the first tube into the female features of the second tube, the two tubes may be joined very similar to the manner described above with respect to fluid reservoir 303.

Figure 5A:
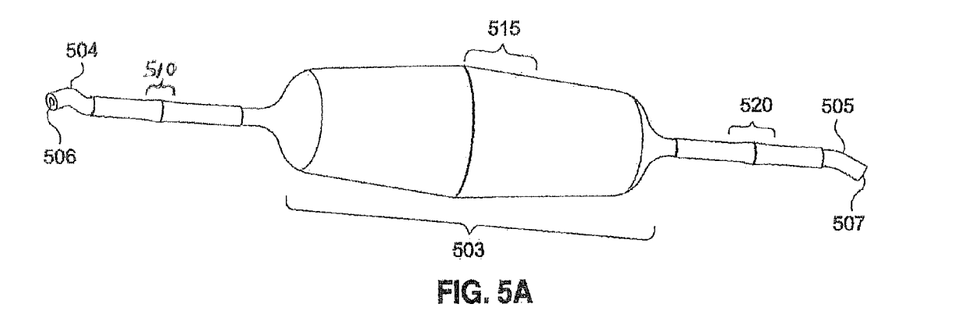
FIG. 5A illustrates a fluid reservoir connected to tubing on both ends according to an embodiment of the present invention.

FIG. 5A illustrates how the concepts of the self-locking and self-sealing mechanical interlocks as applied to a reservoir and the tubing may be applied in combination to eliminate the need for metal or plastic connectors. As shown, three distinct interlocks 510, 515 and 520 may be employed to connect a reservoir 503 with a pair of tubes 504 and 505 (one on each side of the reservoir 503) to create a self-sealing, self-locking fluid path able to transfer fluid from one end 506 of the first tubing 504 to a distal end 507 of the second tubing 505. In one embodiment, the end 506 may lead to an inflatable portion of the gastric band, while the other end 507 may lead to an access port. Or, where the reservoir 503 is only attached to the access port, the reservoir 503 may be attached to the tubing on one end (e.g., end 506) while closed at the other end.

Figure 5B:
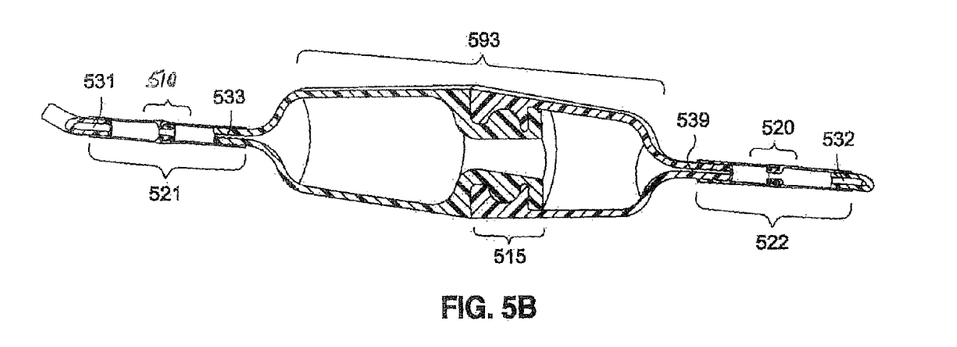
FIG. 5B illustrates a cross-sectional view of the fluid reservoir-tubing system of FIG. 5A according to an embodiment of the present invention.

FIG. 5B is a cross-sectional view of the system of FIG. 5A illustrating the three interlocked joints 510, 515 and 520 functioning in unison to create the self-sealing, self-locking fluid path able to transfer fluid from one end 506 of the first tubing 504 to a distal end 507 of the second tubing 505. Also shown in this view is how the sleeves 521 and 522 may be overmolded on not only the tube portions 531 and 532, respectively, but also over the end portions 533 and 534 of the reservoir 503.

Figure 5C:
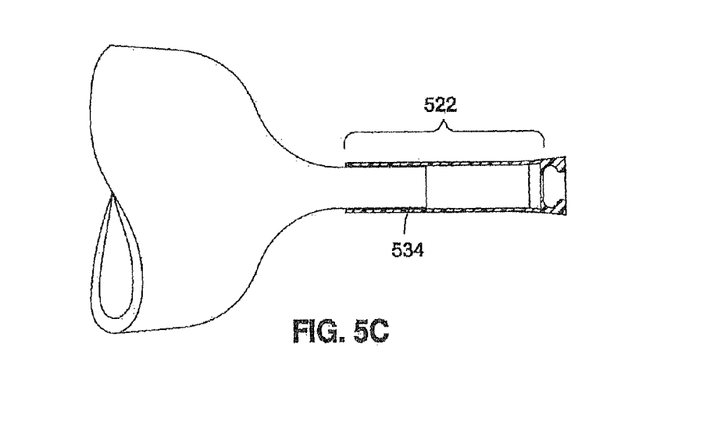
FIG. 5C illustrates a close-up view of a portion of the reservoir-tubing system of FIG. 5A according to an embodiment of the present invention.

As an example, FIG. 5C illustrates a close-up view of the portion of the sleeve 522 overmolded on the end portion 534 of the reservoir 503, thus eliminating the need for a connector or an adhesive.

It should be appreciated that the over-molding and/or the geometrical joint interlocks can be applied to a number of different components not explicitly described herein. Moreover, the geometrical shapes and the number of interlocks utilized to joint together a component or to join one component with another component may also be altered while still being within the spirit and scope of the invention.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A gastric banding system for the treatment of obesity, the gastric banding system comprising:
    a gastric band having an inflatable portion configured to constrict a stomach of a patient;
    an access port coupled to the gastric band for insertion of fluid to or removal of fluid from the inflatable portion of the gastric band to adjust the constriction of the inflatable portion of the gastric band about the stomach of the patient;
    a fluid reservoir for holding fluid and connected between the gastric band and the access port, the fluid reservoir including a first end and a second end, the fluid reservoir having a first male half and a first female half, the first male half extending from a first outer end to a first inner end and the first female half extending from a second outer end to a second inner end,
    the first male half of unitary construction having a first ring and a first flange, the first ring having a first side that faces the first flange and having a second side opposite the first side that faces the first outer end, the first flange located at the first inner end of the first male half and the first ring spaced between the first flange and the first outer end, and
    the first female half defining a first circumferential groove for receiving the first ring and for surrounding the first and second sides of the first ring, and further defining a first annular wall facing the second outer end that seals with the first flange,
    wherein when the first ring extends into and is surrounded by the first groove, and when the first annular wall seals with the first flange, physical interference between the first ring and the first groove and between the first flange and the first annular wall cause the first male half and the first female half to form a first interlock therebetween;
    a first tube for carrying fluid between the inflatable portion of the gastric band and the fluid reservoir, the first tube having a first end connected to the inflatable portion of the gastric band and a second end connected to the first end of the fluid reservoir; and
    a second tube for carrying fluid between the access port and the fluid reservoir, the second tube having a first end connected to the second end of the fluid reservoir and a second end connected to the access port,
    wherein the first interlock creates a fluid tight seal.

2. The gastric banding system of claim 1 wherein when the first male half and the first female half are interlocked, the fluid reservoir is self-sealed.

3. The gastric banding system of claim 1 wherein the fluid reservoir defines three fluidly coupled sub-reservoirs when the first male half and the first female half are interlocked.

4. The gastric banding system of claim 3 wherein a first and a second sub-reservoir are defined by the first male half and the third sub-reservoir is defined by the first female half.

5. The gastric banding system of claim 4 wherein the second sub-reservoir is located between the first sub-reservoir and the third sub-reservoir.

6. The gastric banding system of claim 5 wherein when the second sub-reservoir is filled with fluid, a resultant force presses the first ring into the first groove and presses the first flange against the first annular wall further sealing the reservoir and preventing leaking.

7. The gastric banding system of claim 5, wherein the first flange extends into the third sub-reservoir.

8. The gastric banding system of claim 5, wherein the second sub-reservoir tapers from opposite ends.

9. The gastric banding system of claim 4, wherein the second sub-reservoir defines a cavity having an hourglass shape.

10. The gastric banding system of claim 1 further comprising a second interlock and a first sleeve, wherein the first tube is connected to the fluid reservoir via the second interlock and the first sleeve is overmolded on the second interlock, a portion of the first tube and a portion of the fluid reservoir.

11. The gastric banding system of claim 10 wherein the second interlock fluidly couples the first tube and the fluid reservoir and comprises a second male half and a second female half, the second male half having a second ring and a second flange, the second female half defining a second groove for receiving the second ring, and further defining a second annular wall for sealing with the second flange.

12. The gastric banding system of claim 11 further comprising a third interlock and a second sleeve, wherein the second tube is connected to the fluid reservoir via the third interlock and the second sleeve is overmolded on the third interlock, a portion of the second tube and a portion of the fluid reservoir.

13. The gastric banding system of claim 12 wherein the third interlock fluidly couples the second tube and the fluid reservoir and comprises a third male half and a third female half, the third male half having a third ring and a third flange, the third female half of the third interlock defining a third groove for receiving the third ring, and further defining a third annular wall for sealing with the third flange.

14. The gastric banding system of claim 1, wherein the first circumferential groove is defined by a first sidewall and a second sidewall facing the first sidewall, and wherein when the first male half and the first female half are interlocked, the first ring extends into the groove and the first sidewall is adjacent to the first side of the ring and the second sidewall is adjacent to the second side of the ring.

15. A fluid reservoir for carrying fluid within a gastric banding system for the treatment of obesity, the fluid reservoir comprising:
   a first half of the fluid reservoir of unitary construction including:
      a first connector for fluidly connecting the fluid reservoir to an inflatable portion of a gastric band,
      a first housing coupled to the connector, the first housing defining a first sub-reservoir, the first housing extending to a first flat joining surface, and
      a ring and flange coupled to the first flat joining surface, the ring and flange defining a second sub-reservoir, the ring spaced between the first flat joining surface and the flange, the ring having a first side that faces the flange and having a second side opposite the first side that faces the first flat joining surface; and
   a second half of the fluid reservoir including:
      a second connector for fluidly connecting the fluid reservoir to an access port, and
      a second housing coupled to the second connector, the second housing defining a third sub-reservoir, the second housing tapering to a second flat joining surface, the second housing further defining a circumferential groove for receiving the ring and for surrounding the first and second sides of the ring and defining an annular wall facing a direction opposite the second flat joining surface that seals with the flange,
   wherein when the ring extends into and is surrounded by the groove, and when the annular wall seals with the flange, physical interference between the ring and the groove and between the flange and the annular wall cause the first half and the second half to form a first interlock therebetween.

16. The fluid reservoir of claim 15 wherein when the first half of the fluid reservoir is interlocked with the second half of the fluid reservoir, a fluid path is established between the first sub-reservoir, the second sub-reservoir and the third sub-reservoir.

17. The fluid reservoir of claim 15 wherein the first housing and the second housing are constructed out of rubber silicone and wherein the first connector and the second connector are constructed out of a metal.

18. The fluid reservoir of claim 15 wherein when the second sub-reservoir is filled with fluid, a resultant force presses the ring into the groove and presses the annular wall against the flange further sealing the fluid reservoir and preventing leaking.

19. The fluid reservoir of claim 15, wherein the flange extends into the third sub-reservoir.

20. The fluid reservoir of claim 15, wherein the second sub-reservoir is between the first sub-reservoir and the third sub-reservoir when the first half is interlocked with the second half.

21. A tube-to-tube apparatus for establishing a fluid path between a first tube and a second tube to allow the tubes to carry fluid within a gastric banding system for the treatment of obesity, the apparatus comprising:
   a first sleeve of unitary construction including:
      a first end overmolding the first tube,
      an intermediate portion coupled to the first end, the intermediate portion defining a first sub-reservoir and having a first flat joining surface, and
      a second end having a ring and a flange, the second end protruding from the first flat joining surface and defining a second sub-reservoir fluidly coupled to the first sub-reservoir, the ring spaced between the flange and the first flat joining surface, the ring having a first side that faces the flange and having a second side opposite the first side that faces the first flat joining surface; and
   a second sleeve interlocked to the first sleeve, the second sleeve including:
      a first end of the second sleeve overmolding the second tube,
      an intermediate portion coupled to the first end of the second sleeve, the intermediate portion defining a third sub-reservoir and having a second flat joining surface for interfacing with the first flat joining surface, and
      a second end of the second sleeve defining a circumferential groove for receiving the ring and for surrounding the first and second sides of the ring and defining an annular wall facing a direction opposite that of the second flat joining surface that seals with the flange
   wherein when the ring extends into and is surrounded by the groove, and when the annular wall seals with the flange, physical interference between the ring and the groove and between the flange and the annular wall cause the first sleeve and the second sleeve to form a first interlock therebetween.

22. The apparatus of claim 21 wherein when the first sleeve is interlocked with the second sleeve, a fluid path is established between the first tube and the second tube via the first sub-reservoir, the second sub-reservoir and the third sub-reservoir.

23. The apparatus of claim 21 wherein the first sleeve and the second sleeve are constructed out of rubber silicone.

24. The apparatus of claim 21 wherein when the second sub-reservoir is filled with fluid, a resultant force presses the ring into the groove and presses the flange against the annular wall further sealing the interlock and preventing leaking.

25. The fluid reservoir of claim 21, wherein the flange extends into the third sub-reservoir.

26. The fluid reservoir of claim 21, wherein the second sub-reservoir is between the first sub-reservoir and the third sub-reservoir when the first sleeve is interlocked with the second sleeve.

27. The fluid reservoir of claim 26, wherein the diameter of the second sub-reservoir is smaller than the diameter of the first sub-reservoir and is smaller than the diameter of the third sub-reservoir.

* * * * *